(12) United States Patent  
Hwang et al.

(10) Patent No.: US 11,272,276 B2
(45) Date of Patent: Mar. 8, 2022

(54) PORTABLE BLUETOOTH SPEAKER DEVICE HAVING COMPLEX FUNCTIONS

(71) Applicant: EMSONIC CORP., Gumi-si (KR)

(72) Inventors: Woon Gue Hwang, Siheung-si (KR); Jae Jin Kim, Siheung-si (KR)

(73) Assignee: EMSONIC CORP.

(*) Notice: Subject to any disclaimer, the term of this patent is extended or adjusted under 35 U.S.C. 154(b) by 399 days.

(21) Appl. No.: 16/463,360

(22) PCT Filed: Mar. 22, 2019

(86) PCT No.: PCT/KR2019/003350
§ 371 (c)(1),
(2) Date: May 22, 2019

(87) PCT Pub. No.: WO2020/166758
PCT Pub. Date: Aug. 20, 2020

(65) Prior Publication Data
US 2021/0337290 A1 Oct. 28, 2021

(30) Foreign Application Priority Data
Feb. 11, 2019 (KR) .................. 10-2019-0015310

(51) Int. Cl.
H04W 4/80 (2018.01)
G01S 19/14 (2010.01)
(Continued)

(52) U.S. Cl.
CPC .......... H04R 1/028 (2013.01); F21V 33/0056 (2013.01); G01N 33/004 (2013.01);
(Continued)

(58) Field of Classification Search
CPC ..... H04R 1/028; H04R 2420/07; H04W 4/80; F21V 33/0056; G01N 33/004; G01S 19/14; F21Y 2115/10
(Continued)

(56) References Cited

U.S. PATENT DOCUMENTS

2014/0031082 A1* 1/2014 Zishaan ............ H04M 1/72454
455/556.1
2014/0107915 A1* 4/2014 Yang ................. G01C 21/3626
701/425
2015/0063619 A1* 3/2015 Wenger ............... H04R 1/026
381/334

FOREIGN PATENT DOCUMENTS

KR 10-1771974 B1 8/2017
KR 10-2019-0015310 A 2/2019

* cited by examiner

Primary Examiner — Vivian C Chin
Assistant Examiner — Friedrich Fahnert
(74) Attorney, Agent, or Firm — Lucas & Mercanti, LLP

(57) ABSTRACT

A portable Bluetooth speaker device having complex functions is provided. The speaker device including: a Bluetooth receiver receiving voice information data; a GPS receiver receiving latitude, longitude, and altitude information using a plurality of global positioning system (GPS) satellites to obtain current location information data; a carbon monoxide detector detecting carbon monoxide concentration in air; a display unit displaying the current location information data and a current carbon monoxide concentration value on a display screen; a power amplifier amplifying the voice information data to a predetermined amplification level; a voice output unit outputting the amplified voice information data; a controller configured to receive the voice information data and transmit the received voice information data to the power amplifier and to control such that the current location information data and the current carbon monoxide concen-
(Continued)

tration value are displayed on the display screen; and a power supply unit supplying necessary power to the respective units.

13 Claims, 2 Drawing Sheets

(51) Int. Cl.
    *H04R 1/02*     (2006.01)
    *F21V 33/00*     (2006.01)
    *G01N 33/00*     (2006.01)
    *F21Y 115/10*     (2016.01)

(52) U.S. Cl.
    CPC ............... *G01S 19/14* (2013.01); *H04W 4/80* (2018.02); *F21Y 2115/10* (2016.08); *H04R 2420/07* (2013.01)

(58) Field of Classification Search
    USPC ........................ 381/334; 701/425; 455/556.1
    See application file for complete search history.

PORTABLE BLUETOOTH SPEAKER DEVICE HAVING COMPLEX FUNCTIONS

CROSS-REFERENCE TO RELATED APPLICATIONS

This application is a 371 U.S. national stage of PCT/KR2019/003350, filed Mar. 22, 2019 which claims the priority from Korean Patent Application No. 10-2019-0015310, filed Feb. 11, 2019, the contents of each of which are incorporated herein by reference.

TECHNICAL FIELD

The present invention relates to a portable Bluetooth speaker device, which outputs sound via wireless connection with a user terminal and has complex functions.

BACKGROUND ART

In general, Bluetooth refers to a short-range wireless technology standard, which connects mobile devices such as mobile phones, notebooks, earphones, headphones, and the like and allows information to be exchanged therebetween. Bluetooth is used in electronic devices that need a low-power wireless connection to communicate over very short-range, typically within about 10 meters.

For example, with a Bluetooth headset, a user can listen to music from a MP3 player in a pocket without the hassle of cables. Meanwhile, as smartphones and tablet PCs have become popular, people can enjoy movies and music through smartphones and tablet PCs at any place.

However, smartphones and tablet PCs are unable to reproduce high-quality sound due to limitations of built-in micro-speakers. To overcome such a drawback, Bluetooth speakers connected to smartphones or tablet PCs via Bluetooth can be used.

A Bluetooth speaker is a device which is equipped with a Bluetooth function for outputting sound and is connected to a mobile terminal carried by a user, such as a smartphone, a tablet PC, a notebook PC, and a MP3 player to output audio of music files played on the mobile terminal through the speaker.

Such a Bluetooth speaker is mainly used for outdoor activities and camping. A Bluetooth speaker proposed in the related art is problematic in that it is inconvenient to carry and store as well as to carry and mount. In particular, there is no special function other than a unique function, and thus it is necessary to prepare items such as a gas detector, a lighting device, and the like in the case of outdoor activities and camping, and which may become a burden. As described above, the Bluetooth speaker in the related art does not have various functions, and thus there has been a demand for improving user functionality.

DISCLOSURE

Technical Problem

Accordingly, the present invention has been made keeping in mind the above problems occurring in the related art, and an objective of the present invention is to provide a portable Bluetooth speaker device having complex functions, wherein the speaker device is configured to output sound via wireless connection with a user terminal, while providing complex functions including a current location acquisition function using GPS reception, a carbon monoxide detection function, an LED light output function, a fine dust detection function, an ultrafine dust detection function, and the like, thus being easy to use for outdoor activities or camping and improving user convenience.

Technical Solution

In order to accomplish the above objective, the present invention provides a portable Bluetooth speaker device having complex functions, the speaker device including: a Bluetooth receiver provided inside a main body that defines a body of the speaker device, and receiving voice information data from an external terminal via Bluetooth communication; a GPS receiver provided inside the main body and receiving latitude, longitude, and altitude information using a plurality of global positioning system (GPS) satellites to obtain current location information data; a carbon monoxide detector provided at a side of the main body and detecting carbon monoxide (CO) concentration in air; a display unit provided at a side of the main body and displaying the current location information data obtained by the GPS receiver and a current carbon monoxide concentration value detected by the carbon monoxide detector on a display screen; a power amplifier provided inside the main body and amplifying the voice information data received from the Bluetooth receiver to a predetermined amplification level; a voice output unit provided at a side of the main body and outputting the amplified voice information data from the power amplifier; a controller provided inside the main body, and configured to receive the voice information data from the Bluetooth receiver and transmit the received voice information data to the power amplifier such that a user can audibly perceive the voice information data through the voice output unit and to control such that the current location information data obtained by the GPS receiver and the current carbon monoxide concentration value detected by the carbon monoxide detector are displayed on the display screen of the display unit so as to be visually perceived by the user; and a power supply unit provided inside the main body and supplying necessary power to the respective units.

The controller may receive the current carbon monoxide concentration value detected by the carbon monoxide detector and compare the current carbon monoxide concentration value with a predetermined reference concentration value, and when the current carbon monoxide concentration value is greater than the reference concentration value, the controller may control operation of the power amplifier and the voice output unit to output a predetermined gas alarm sound at the predetermined amplification level, thus allowing the user to audibly perceive the alarm sound.

When the gas alarm sound is continuously output through the voice output unit for a predetermined period of time or longer, the controller may control operation of the power amplifier and the voice output unit to output the gas alarm sound at a maximum amplification level, thus allowing the user to audibly perceive the alarm sound with help of people nearby.

The speaker device may further include a user input unit provided at a side of the main body and outputting a specific user input signal in response to user manipulation.

When the controller receives the specific user input signal from the user input unit while the gas alarm sound is output through the voice output, the controller may control operation of the power amplifier and the voice output unit such that output of the gas alarm sound is canceled.

The speaker device may further include: a user input unit provided at a side of the main body and outputting a specific user input signal in response to user manipulation; and an LED lighting unit provided inside or outside the main body and outputting LED light having at least one color.

The controller may control operation of the LED lighting unit such that a brightness or on-off state of the LED lighting unit is changed in response to a specific user input signal.

The speaker device may further include: an LED lighting unit provided inside or outside the main body and outputting LED light having at least one color; and an illuminance sensor provided at a side of the main body and detecting external brightness information.

The controller may receive the external brightness information detected by the illuminance sensor, process the detected external brightness information to obtain an external brightness value, and control operation of the LED lighting unit such that the brightness or on-off state of the LED lighting unit is changed in response to the obtained external brightness value.

The controller may control operation of the power amplifier and the voice output unit such that a predetermined distress occurrence signal is output through the voice output unit in response to a specific user input signal that is output from the user input unit when a distress occurs.

The power supply unit may include: at least one battery; and a charging circuit unit receiving external power through a charging terminal mounted at a side of the main body and charging the battery of the power supply unit under control of the controller.

The controller may continuously monitor a battery power level of the power supply unit and control such that the monitored battery power level is displayed on the display screen of the display unit.

The speaker device may further include: a user input unit provided at a side of the main body and outputting a specific user input signal in response to user manipulation; and a wireless communication unit wirelessly transmitting a predetermined distress occurrence signal to the external terminal by using a wireless communication method.

The controller may control operation of the wireless communication unit such that the predetermined distress occurrence signal is wirelessly transmitted to the external terminal in response to the specific user input signal output from the user input unit when a distress occurs, together with the current location information data obtained by the GPS receiver through the wireless communication unit.

The wireless communication method may be any one of short-range wireless communication methods including Bluetooth, ZigBee, ultra-wideband (UWB), radio-frequency identification (RFID), and infrared (IR), or any one of long-range wireless communication methods including 3G, 4G, 5G, wireless fidelity (Wi-Fi), wireless gigabit alliance (WiGig), wireless broadband internet (Wibro), and world interoperability for microwave access (Wimax).

The external terminal may be at least one of mobile terminal devices including a smartphone, a smart pad, and a smart note.

The speaker device may further include: a fine dust detector provided inside or outside the main body and detecting fine dust concentration in air; and an ultrafine dust detector provided inside or outside the main body and detecting ultrafine dust concentration in air.

The controller may control such that a current fine dust concentration value and a current ultrafine dust concentration value, which are respectively detected by the fine dust detector and the ultrafine dust detector, are displayed on the display screen of the display unit so as to be visually perceived by the user.

The fine dust detector may measure fine dust having a particle size of equal to or less than 10 μm, and the fine dust detector includes at least one sensor for measuring at least one of air pollutants including sulfur dioxide, nitrogen oxide, lead, and ozone.

The ultrafine dust detector may measure ultrafine dust having a particle size of equal to or less than 2.5 μm, and the ultrafine dust detector includes at least one ultrafine dust sensor for measuring total carbon, organic carbon, and elemental carbon contained in ultrafine dust.

Advantageous Effects

According to the portable Bluetooth speaker device having complex functions as described above, it is possible to output sound via wireless connection with the user terminal, while providing complex functions including a current location acquisition function using GPS reception, a carbon monoxide detection function, an LED light output function, a fine dust detection function, an ultrafine dust detection function, and the like. Therefore, the present invention can be used for outdoor activities or camping and improve user convenience.

BEST MODE

Figure 1:
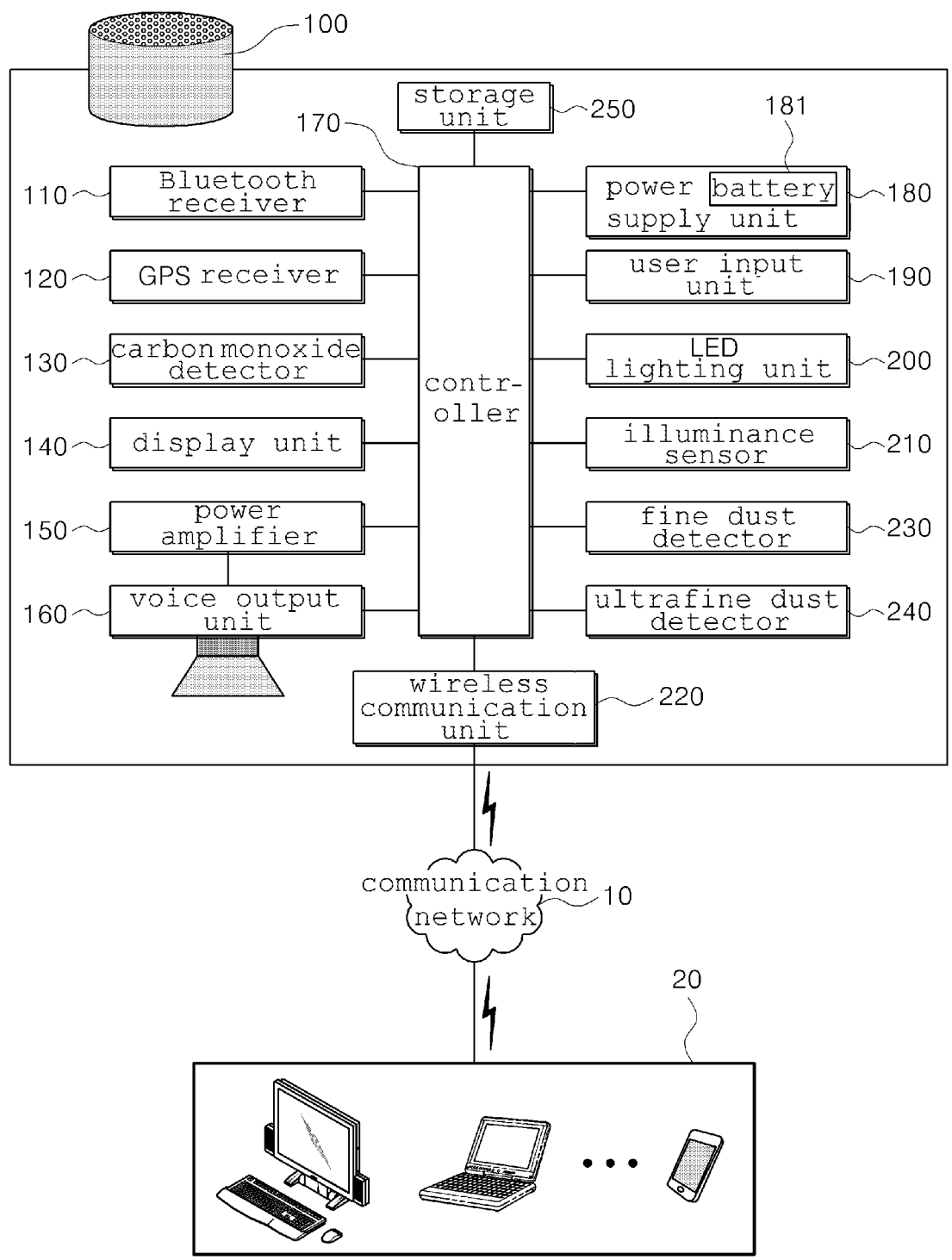
FIG. 1 is a block diagram showing a portable Bluetooth speaker device having complex functions according to an embodiment of the present invention.

The above and other objectives, features and advantages of the present invention will be more clearly understood from the following detailed description taken in conjunction with the accompanying drawings, such that the invention can be easily embodied by one of ordinary skill in the art to which this invention belongs. In the following description, it is to be noted that, when the functions of conventional elements and the detailed description of elements related with the present invention may make the gist of the present invention unclear, a detailed description of those elements will be omitted.

It will be understood that, although the terms first, second, etc. may be used herein to describe various elements, these elements should not be limited by these terms. These terms are only used to distinguish one element, from another element. For instance, a first element discussed below could be termed a second element without departing from the teachings of the present invention. Similarly, the second element could also be termed the first element. The terminology used herein is for the purpose of describing particular embodiments only and is not intended to be limiting of example embodiments of the invention. As used herein, the singular forms "a", "an", and "the" are intended to include the plural forms as well, unless the context clearly indicates otherwise.

Although terminologies used in the present specification are selected from general terminologies used currently and widely in consideration of functions, they may be changed in accordance with intentions of technicians engaged in the corresponding fields, customs, advents of new technologies and the like. Occasionally, some terminologies may be arbitrarily selected by the applicant(s). In this case, the meanings of the arbitrarily selected terminologies shall be described in the corresponding part of the detailed description of the specification. Therefore, terminologies used in the present specification need to be construed based on the substantial meanings of the corresponding terminologies and the overall matters disclosed in the present specification rather than construed as simple names of the terminologies.

Unless the context clearly indicates otherwise, it will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Also, the terms "~part", "~unit", "module", "apparatus" and the like mean a unit for processing at least one function or operation and may be implemented by a combination of hardware and/or software.

Hereinbelow, exemplary embodiments of the present invention will be described in detail with reference to the accompanying drawings. Various changes to the following embodiments are possible and the scope of the present invention is not limited to the following embodiments. It should be understood that the embodiments of the present invention are presented to make complete disclosure of the present invention and help those who are ordinarily skilled in the art best understand the invention.

Combinations of blocks in the accompanying block diagrams may be executed by computer program instructions (execution engine), and the computer program instructions may be mounted in a processor of a general-use computer, special-use computer, or other programmable data processing equipment. Thus, the instructions executed through the processor of the computer or other programmable data processing equipment generate units for performing functions described in the respective blocks of the block diagrams. The computer program instructions can be stored in a computer usable or readable memory oriented to a computer or other programmable data processing equipment, in order to implement functions in a specific method. Thus, the instructions stored in the computer usable or readable memory can be used to manufacture products including instruction units for performing the functions described in the respective blocks of the block diagrams.

As described above, the computer program instructions can be mounted in the computer or other programmable data processing equipment. Therefore, instructions which generate processes by performing a series of operation steps on the computer or other programmable data processing equipment and operate the computer or other programmable data processing equipment can provide steps for executing the functions described in the respective blocks of the block diagrams.

Each of the blocks may indicate a part of a module, segment or code including one or more executable instructions for executing specific logical functions. In some substitutions, the functions described in the blocks can be performed out of sequence. That is, two blocks can be operated or performed substantially at the same time, and the blocks can be operated or performed in the reverse order of the corresponding function.

Figure 2:
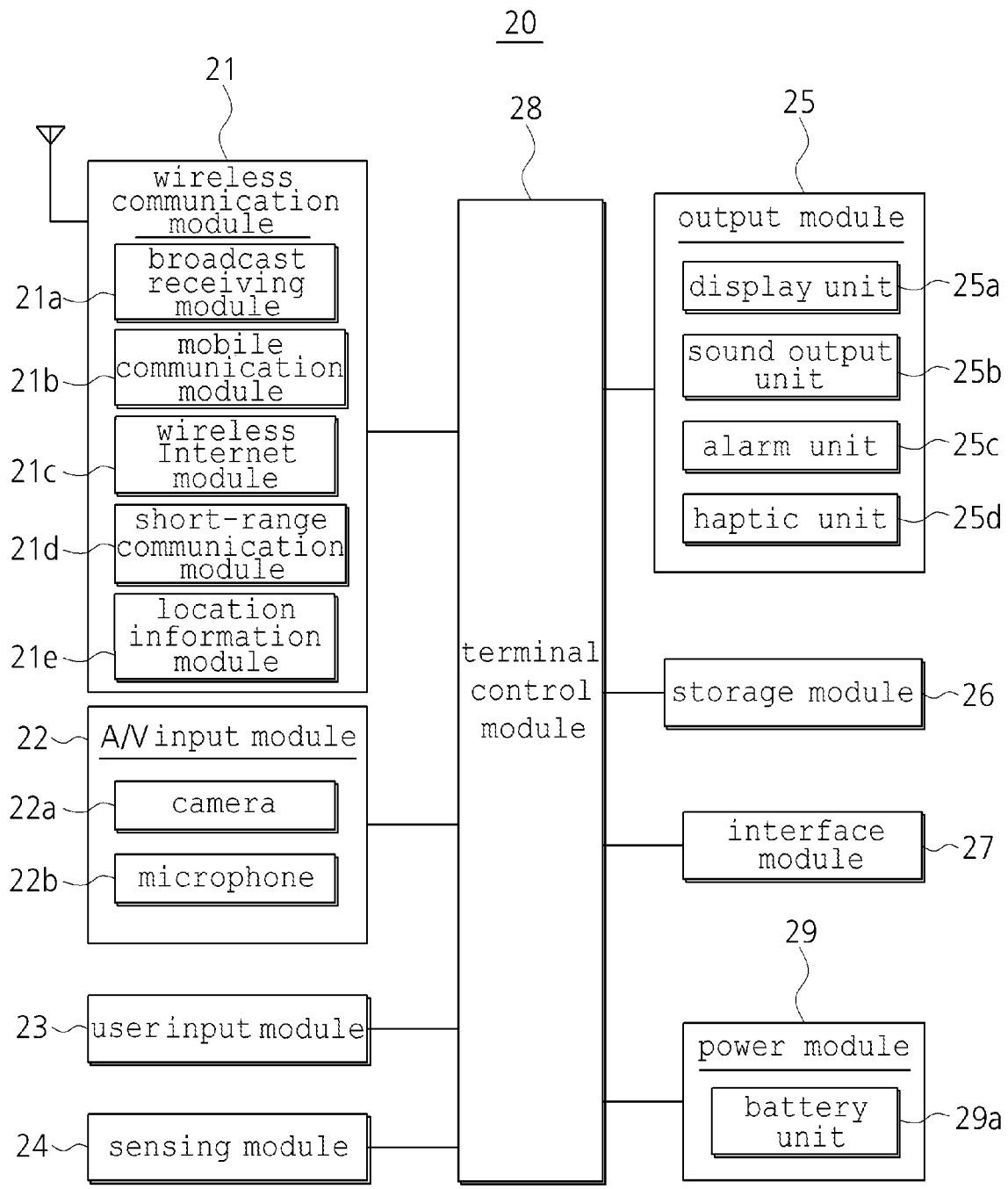
FIG. 2 is a detailed block diagram showing an external terminal applied to an embodiment of the present invention.

FIG. 1 is a block diagram showing a portable Bluetooth speaker device having complex functions according to an embodiment of the present invention, and FIG. 2 is a detailed block diagram showing an external terminal applied to the embodiment of the present invention.

Referring to FIGS. 1 and 2, a portable Bluetooth speaker device having complex functions according to an embodiment of the present invention largely includes a main body 100, a Bluetooth receiver 110, a GPS receiver 120, a carbon monoxide detector 130, a display unit 140, a power amplifier 150, an voice output unit 160, a controller 170, and a power supply unit 180. Furthermore, the portable Bluetooth speaker device having complex functions according to the embodiment of the present invention may further include a user input unit 190, an LED lighting unit 200, an illuminance sensor 210, a wireless communication unit 220, a fine dust detector 230, an ultrafine dust detector 240, and/or a storage unit 250. Meanwhile, the components illustrated in FIGS. 1 and 2 are not essential, and the portable Bluetooth speaker device having complex functions according to the embodiment of the present invention may have more or fewer components.

Hereinafter, the components of the portable Bluetooth speaker device having complex functions according to the embodiment of the present invention will be described in detail.

The main body 100 defines a body of the speaker device, and it is preferable that the main body is constructed such that each unit to be described later, that is, the Bluetooth receiver 110, the GPS receiver 120, the carbon monoxide detector 130, the display unit 140, the power amplifier 150, the voice output unit 160, the controller 170, the power supply unit 180, the user input unit 190, the LED lighting unit 200, the illuminance sensor 210, the wireless communication unit 220, the fine dust detector 230, the ultrafine dust detector 240, and/or the storage unit 250, are built in or mounted on the inside/outside thereof. The main body 100 is provided in various forms according to user preference such that a user can easily carry it.

The Bluetooth receiver 110 is provided inside the main body 100 and functions to receive voice information data from an external terminal 20 by using Bluetooth communication under control of the controller 170, and transmit the received voice information data to the controller 170.

The GPS receiver 120 is provided inside the main body 100 and functions to receive latitude, longitude, and altitude information using a plurality of global positioning system (GPS) satellites under control of the controller 170 to obtain current location information data, and transmit the obtained current location information data to the controller 170.

Meanwhile, in the embodiment of the present invention, it is preferable that a signal emitted from a GPS satellite is received through the GPS receiver 120, and a distance to the satellite is calculated on the basis of a difference between reference time and signal transmission time to obtain altitude above sea level information of the current location, but the present invention is not limited thereto. For example, the altitude above sea level of the current location may be measured using a pressure altimeter that indicates the altitude calculated by comparing the current pressure with the standard pressure, a sonic altimeter that measures the altitude by measuring the time taken for sound waves emitted from the ground to travel and back to the ground after reflection and measuring the speed of the sound waves, and a radio altimeter that uses a pulse of radio frequency, and the like.

The carbon monoxide detector 130 is provided at a side of the main body 100 and functions to detect the concentration of carbon monoxide in the air under control of the controller 170, and transmit a sensing result to the controller 170.

The display unit 140 is provided at a side of the main body 100 and functions to display the current location information data obtained by the GPS receiver 120 on a display screen under control of the controller 170.

Furthermore, the display unit 140 functions to display a current carbon monoxide concentration value detected by the carbon monoxide detector 130 on the display screen under control of the controller 170.

Furthermore, the display unit 140 functions to display a current fine dust concentration value and a current ultrafine dust concentration value that are respectively detected by the fine dust detector 230 and the ultrafine dust detector 240 on the display screen under control of the controller 170.

The display unit 140 includes at least one of a liquid crystal display (LCD), a light emitting diode (LED), a thin film transistor liquid crystal display (TFT LCD), an organic light emitting diode (OLED), a flexible display, a plasma display panel (PDP), alternate lighting of surfaces (ALiS), digital light processing (DLP), liquid crystal on silicon (LCoS), a surface-conduction electron-emitter display (SED), a field-emission display (FED), laser TV (quantum dot laser, liquid crystal laser), ferro-electric liquid display (FLD), interferometric modulator display (iMoD), thick-dielectric electroluminescence (TDEL), a quantum dot display (QD-LED), telescopic pixel display (TPD), an organic light-emitting transistor (OLET), laser-powered phosphor display (LPD), a holographic display, and a three-dimensional (3d) display. However, the present invention is not limited to this, but includes any one capable of displaying numbers, characters, figures, images, and the like.

The power amplifier 150 is provided inside the main body 100 and functions to amplify the voice information data receive from the Bluetooth receiver 110 to a predetermined amplification level under control of the controller 170 such that the user can listen and transmit the amplified data to the voice output unit 160.

The voice output unit 160 is provided at a side of the main body 100 and functions to output the amplified voice information data from the power amplifier 150 under control of the controller 170.

It is preferable that the voice output unit 160 is implemented as a conventional speaker, but is not limited thereto. The voice output unit may be implemented as a voice amplifier circuit, connection jack, or the like such that the user can listen through earphones or headphones.

The controller 170 is provided inside the main body 100 and performs overall control of the portable Bluetooth speaker device having complex functions according to the embodiment of the present invention. In particular, the controller functions to receive the voice information data from the Bluetooth receiver 110, and transmit the received voice information data to the power amplifier 150 such that the user can audibly perceive the voice information data through the voice output unit 160.

Furthermore, the controller 170 controls such that the current location information data obtained by the GPS receiver 120 and the current carbon monoxide concentration value detected by the carbon monoxide detector 130 are displayed on a display screen of the display unit 140 so as to be visually perceived by the user.

Furthermore, the controller 170 receives the current carbon monoxide concentration value detected by the carbon monoxide detector 130 and compares the current carbon monoxide concentration value with a predetermined reference concentration value. Then, when the current carbon monoxide concentration value is greater than the reference concentration value, the controller controls operation of the power amplifier 150 and the voice output unit 160 to output a predetermined gas alarm sound at a predetermined amplification level, thus allowing the user to audibly perceive the alarm sound.

Furthermore, when the gas alarm sound is continuously output through the voice output unit 160 for a predetermined period of time or longer, the controller 170 controls operation of the power amplifier 150 and the voice output unit 160 such that to output the gas alarm sound at a maximum amplification level, thus allowing the user to audibly perceive the alarm sound with the help of people nearby.

Furthermore, when the controller 170 receives a specific user input signal (for example, a gas warning cancellation signal) from the user input unit 190 while the gas alarm sound is output through the voice output unit 160, the controller controls operation of the power amplifier 150 and the voice output unit 160 such that output of the gas alarm sound is canceled.

Furthermore, the controller 170 controls operation of the LED lighting unit 200 such that the brightness and/or on-off state of the LED lighting unit 200 is changed in response to a specific user input signal (for example, a lighting brightness signal and/or a lighting on-off signal).

Furthermore, the controller 170 receives external brightness information detected by the illuminance sensor 210, processes the external brightness information to obtain an external brightness value, and controls operation of the LED lighting unit 200 such that the brightness and/or on-off state of the LED lighting unit 200 is changed in response to the obtained external brightness value.

Furthermore, the controller 170 controls operation of the power amplifier 150 and the voice output unit 160 such that a predetermined distress occurrence signal is output through the voice output unit 160 in response to a specific user input signal (for example, a distress occurrence input signal) that is output from the user input unit 190 when a distress occurs.

Furthermore, the controller 170 continuously monitors a battery power level of the power supply unit 180 and controls such that the monitored battery power level is displayed on the display screen of the display unit 140.

Furthermore, the controller 170 controls such that the current fine dust concentration value and/or the current ultrafine dust concentration value, which are respectively detected by the fine dust detector 230 and/or the ultrafine dust detector 240, are displayed on the display screen of the display unit 140 so as to be visually perceived by the user.

Furthermore, the controller 170 controls operation of the wireless communication unit 220 such that the predetermined distress occurrence signal is wirelessly transmitted to the external terminal 20 or a user terminal through the communication network 10 in response to the specific user input signal output from the user input unit 190 when a distress occurs, together with the current location information data obtained by the GPS receiver 120 through wireless communication unit 220.

Herein, the network 10 may be, for example, an Ethernet, a mobile network, or the like. The network may be a large high-speed network that enables large-capacity, long-distance voice and data services, or Internet, or a next-generation wireless network including wireless fidelity (Wi-Fi), wireless broadband Internet (WiBro), and world interoperability for microwave access (WiMAX) that provides high-speed multimedia services.

The Internet refers to a global open computer network architecture that provides services, such as hypertext transfer protocol (HTTP), Telnet, file transfer protocol (FTP), domain name system (DNS), simple mail transfer protocol (SMTP), simple network management protocol (SNMP), network file service (NFS), network information service (NIS) that exist in the TCP/IP and upper layers thereof. The Internet provides an environment in which the user terminal 20 can be connected to the wireless communication unit 220. Meanwhile, the Internet may be a wired or wireless Internet, or may be a wired public network, a wireless mobile network, or a core network integrated with a portable Internet.

If the network 10 is a mobile network, the mobile network may be a synchronized mobile network or a non-synchronized mobile network. An example of the non-synchronized mobile network includes a wideband code division multiple access (WCDMA) network. In this case, although not shown in the drawings, the mobile network includes a radio network controller (RNC), for example. On the other hand, although the WCDMA network is used as an example, a next generation communication network such as a 3G LTE network, a 4G network, and a 5G network, or an IP network based on IP may be used. The network 10 functions to transmit signals and data between the user terminal 20 and the wireless communication unit 220.

The power supply unit 180 is provided inside the main body 100 and functions to supply power to the above-described units, that is, the Bluetooth receiver 110, the GPS receiver 120, the carbon monoxide detector 130, the display unit 140, the power amplifier 150, the voice output unit 160, the controller 170, the user input unit 190, the LED lighting unit 200, the illuminance sensor 210, the wireless communication unit 220, the fine dust detector 230, the ultrafine dust detector 240, and/or the storage unit 250. Accordingly, it is preferable that the power supply unit is implemented to include a conventional portable battery 181, but is not limited thereto. The power supply unit may be implemented to convert commercial AC power (for example, AC 220V) to DC and/or AC power for continuous power supply.

The power supply unit 180 includes at least one battery 181 and may further include a charging circuit unit that receives external power through a charging terminal (not shown) mounted at a side of the main body 100 and charges the battery 181 of the power supply unit 180 under control of the controller 170.

Furthermore, the power supply unit 180 includes a power management unit (not shown) that functions to protect the components from an external power shock, and output a constant voltage. The power management unit includes an electrostatic damage (ESD) protection device, a power detector, a rectifier, a power breaker, and the like.

Herein, the ESD protection device is configured to protect electrical components from static electricity or sudden power shock. The power detector is configured to transmit a shutdown signal to the power breaker when a voltage outside an allowable voltage range is entered and to transmit a step-up or step-down signal to the rectifier in response to a change in voltage within the allowable voltage range. The rectifier is configured to perform a step-up or step-down rectification operation in response to a signal of the power detector such that a constant voltage is supplied with a minimum variation of an input voltage. The power breaker is configured to shut off power supplied from the battery in response to a shut down signal transmitted from the power detector.

Furthermore, the user input unit 190 is provided at a side of the main body 100 and functions to output a specific user input signal in response to user manipulation.

The user input unit 190 generates input data for controlling operation of the speaker device in response to a user input. The user input unit includes a push switch, a keypad dome switch, a touch input module (constant voltage/capacitance), a jog wheel, a jog switch, and the like.

Although not shown in the drawings, the user input unit 190 includes a key input unit (or a touch input unit that interworks with the display unit 140) having at least one key button, and an input module for driving the key input unit. The user input unit is connected to the controller 170 through a bus to receive input of commands for instructing various processing of the controller 170 or data required for processing of the controller 170.

Furthermore, the LED lighting unit 200 is provided inside and/or outside the main body 100 and functions to output LED light having at least one color under control of the controller 170, and emit the light to the outside.

The LED lighting unit 200 further enhances appearance of the main body 100 by ensuring visibility using a conventional RGB LED light, and enables a colorful effect through the RGB LED light.

The illuminance sensor 210 is provided at a side of the main body 100 and functions to detect external brightness information under control of the controller 170, and transmit the detected external brightness information to the controller 170.

The wireless communication unit 220 is provided inside and/or outside the main body 100 and functions to transmit the predetermined distress occurrence signal to the user terminal 20 by using a wireless communication method under control of the controller 170.

Herein, it is preferable that the wireless communication method is any one of short-range wireless communication methods including Bluetooth, ZigBee, ultra-wideband (UWB), radio-frequency identification (RFID), and infrared (IR), or any one of long-range wireless communication methods including 3G, 4G, 5G, Wi-Fi, wireless gigabit alliance (WiGig), Wibro, and Wimax.

The fine dust detector 230 is provided inside and/or outside the main body 100. The fine dust detecting functions to detect the concentration of fine dust in the air under control of the controller 170, and transmit a detection result to the controller 170.

The fine dust detector 230 is for measuring fine dust having a particle size of equal to or less than 10 μm. It is preferable that the fine dust detecting includes at least one sensor for measuring at least one of air pollutants including sulfur dioxide, nitrogen oxide, lead, and/or ozone.

The ultrafine dust detector 240 is provided inside and/or outside the main body 100. The ultrafine dust detecting functions to detect the concentration of ultrafine dust in the air under the control of the controller 170, and transmit a detection result to the controller 170.

Furthermore, the ultrafine dust detector 240 is for measuring ultrafine dust having a particle size of equal to or less than 2.5 μm. It is preferable that the ultrafine dust detector 240 includes at least one ultrafine dust sensor for measuring total carbon, organic carbon, and elemental carbon contained in ultrafine dust.

The storage unit 250 is provided inside and/or outside the main body 100 and functions to store and maintain at least one program code executed through the controller 170 under control of the controller, and at least one data set used by the program code.

Furthermore, the storage unit 250 functions to receive the current carbon monoxide concentration value detected by the carbon monoxide detector 130 under control of the controller 170, and store and manage, based on this, carbon monoxide concentration values in a database (DB) in units of time and/or day and/or week and/or month and/or quarter and/or year.

Furthermore, the storage unit 250 functions to receive the current fine dust concentration value and/or the current ultrafine dust concentration value, which are respectively detected by the fine dust detector 230 and/or the ultrafine dust detector 240, under control of the controller 170, and store and manage, based on this, fine dust concentration values and/or current ultrafine dust concentration values in a database (DB) in units of time and/or day and/or week and/or month and/or quarter and/or year.

The storage unit 250 includes, for example, at least one type of a storage medium including a flash memory type, a hard disk type, a multimedia card micro type, a card type memory (for example, a SD memory, a XD memory or the like), a random-access memory (RAM), a static random-access memory (SRAM), a read-only memory (ROM), an electrically erasable programmable read-only memory (EE-PROM), a programmable read-only memory (PROM), a magnetic memory, a magnet disk, and an optical disk.

Meanwhile, although not shown in the drawings, the present invention may further include a temperature measuring unit (not shown) and/or a humidity measuring unit (not shown) may be provided inside and/or outside the main body 100 to measure temperature and/or humidity around the main body 100.

In this case, it is preferable that the temperature measuring unit includes at least one temperature measuring sensor (not shown) for measuring the temperature in the air. The temperature measuring sensor is a thermistor device in which the internal resistance value changes in response to an ambient temperature change. The thermistor device may be a negative temperature coefficient (NTC) thermistor, a positive temperature coefficient (PTC) thermistor, or a critical temperature resistor thermistor (CRT).

It is preferable that the temperature measuring sensor is a contact type temperature sensor using a thermistor device, but is not limited thereto. For example, the temperature measuring sensor is a thermocouple sensor, a bimetal, an IC temperature sensor, an infrared sensor which is a non-contact type sensor, or the like.

Furthermore, it is preferable that the humidity measuring unit includes at least one humidity measuring sensor (not shown) for measuring the humidity in the air. The humidity measuring sensor measures the humidity by using a change in electrical properties of a humidity sensitive material due to moisture.

The humidity sensor is largely divided into a resistive humidity sensor and a capacitive type humidity sensor and is widely used to make optimal condition of a home appliance, a mobile phone, a vehicle, a medical device, an air purification system, and an automatic air-conditioning system.

The resistive humidity sensor measures the humidity using a change in resistance in response to humidity. The resistive humidity sensor is widely used due to higher cost competitiveness than the capacitive humidity sensor.

In recent years, however, capacitive humidity sensors are also manufactured in a one-chip form on a semiconductor substrate and thus have a price competitiveness advantage over the resistive humidity sensor, resulting in an increase in use thereof. In particular, the capacitive humidity sensor has excellent reliability, good linearity, and small sensitivity to temperature, which is advantageous over the resistive humidity sensor.

The capacitive humidity sensor, which is a sensor using the principle that the capacitance changes in response to the amount of water molecules adsorbed on a humidity sensitive membrane, operates in the form of a capacitor using a humidity sensitive material, such as polyimide or ceramic in which dielectric constant changes when moisture is absorbed, as a dielectric. That is, the principle is that a humidity sensing layer for sensing the humidity exists, and when moisture permeates through the humidity sensing layer, the dielectric constant changes and thus the capacitance changes.

Various embodiments described herein may be implemented in a computer-readable or similar medium using, for example, software, hardware, or any combination thereof.

For hardware implementation, embodiments described herein may be implemented by using at least one of application-specific integrated circuits (ASICs), digital signal processors (DSPs), digital signal processing devices (DSPDs), programmable logic devices (PLDs), field-programmable gate arrays (FPGAs), processors, controllers, micro-controllers, microprocessors, and electronic units for performing functions. In some cases, such embodiments may be implemented by the controller 170.

For software implementation, embodiments such as procedures or functions described herein may be implemented with a separate software module performing at least one function or operation. Software codes may be implemented by a software application written in an appropriate software language. The software codes may be stored in the storage unit 250 and executed by the controller 170.

Meanwhile, it is preferable that the user terminal 20 applied to the embodiment of the present invention is at least one of mobile terminal devices including a smartphone, a smart pad, and a smart note that communicate through a wireless Internet or a portable Internet. Furthermore, the user terminal may comprehensively denote all wired/wireless home appliances/communication devices having a user interface for connecting to the wireless communication unit 220, such as a portable PC, a notebook PC, a palm PC, mobile play-station, a digital multimedia broadcasting (DMB) phone having a communication function, a tablet PC, an iPad, and the like.

As shown in FIG. 2, the user terminal 20 includes a wireless communication module 21, an audio/video (A/V) input module 22, a user input module 23, a sensing module 24, an output module 25, a storage module 26, an interface module 27, a terminal control module 28, a power module 29, and the like. On the other hand, the components shown in FIG. 2 are not essential, and thus the user terminal 20 may have more or fewer components.

Hereinafter, the components of the user terminal 20 will be described in detail.

The wireless communication module 21 may include at least one module that enables wireless communication between the user terminal 20 and the wireless communication unit 220. For example, the wireless communication module 21 may include a broadcast receiving module 21a, a mobile communication module 21b, a wireless Internet module 21c, a short-range communication module 21d, a location information module 21e, and the like.

The broadcast receiving module 21a receives a broadcast signal (for example, a TV broadcast signal, a radio broadcast signal, a data broadcast signal, and the like) and/or broadcast related information from an external broadcast management server through various broadcast channels (for example, a satellite channel, a terrestrial channel, and the like).

The mobile communication module 21b transmits and receives a wireless signal to and from at least one of a base station, an external terminal, and a server on a mobile communication network. The wireless signal may include various types of data according to a voice call signal, a video call signal, or a text/multimedia message transmission/reception.

The wireless Internet module 21c is a module for wireless Internet access and may be built in or built out of the user terminal 20. Examples of such wireless communication may include WLAN (Wi-Fi), Wibro, Wimax, HSDPA, LTE, and the like.

The short-range communication module 21d is a module for short-range communication. Examples of such short-range communication may include Bluetooth, ZigBee, UWB, RFID, IR, and the like.

The location information module 21e is a module for detecting or obtaining a location of the user terminal 20 and obtains current location information of the user terminal 20 using global positioning system (GPS) or the like.

Meanwhile, the location information module performs data transmission/reception with the wireless communication unit 220 using a specific application program stored in the storage module 26 through the above-described wireless communication module 21 and/or a wired communication module (not shown) under control of the terminal control module 28.

The A/V input module 22 is a module for receiving input of an audio signal or video signal and fundamentally includes a camera 22a, a microphone 22b, and the like. The camera 22a processes image frames of still images or moving images, which are obtained by an image sensor in a video call mode or a capturing mode. The microphone 22b receives an external audio signal through a microphone in a phone call mode, a recording mode, a voice recognition mode, or the like and processes the external audio signal into electric audio data.

The user input unit 23 is a module for generating input data for controlling operation of the user terminal 20. In particular, the user input unit functions to receive input of a selection signal for any one of data management information displayed on a display unit 25a of the output module 25. The user input unit may include a touch panel (constant voltage/capacitance) operated by user's touching or a separate input device (for example, a key pad, dome switch, a jog wheel, a jog switch, and the like).

The sensing module 24 senses a current state of the user terminal 20, such as an open/close state of the user terminal 20, a location of the user terminal 20, a presence or absence of user contact with the terminal, a user touch motion to a specific region, a direction of the user terminal 20, acceleration/deceleration of the user terminal 20, and the like so as to generate a sensing signal for controlling operation of the user terminal 20. The sensing signal is transmitted to the terminal control module 28 and can serves as a basis for the terminal control module 28 to perform a specific function.

The output module 25 is a module for generating visual, auditory, and/or tactile output and fundamentally includes the display unit 25a, a sound output unit 25b, an alarm unit 25c, a haptic unit 25d, and the like.

The display unit 25a outputs information processed in the user terminal 20. For example, when the user terminal 20 is operated in a phone call mode, the display unit displays a user interface (UI) and/or a graphic user interface (GUI), which includes information associated with a phone call. As another example, when the user terminal is operated in a video call mode or a capturing mode, the display unit displays a captured and/or received image, a UI, or a GUI.

The sound output unit 25b may output audio data received from the wireless communication module 21 or stored in the storage module 26 in a call signal receiving mode, a phone call mode or a recording mode, a voice recognition mode, a broadcasting receiving mode and the like.

The alarm unit 25c outputs a signal for indicating generation of an event of the user terminal 20. Examples of the event generated in the user terminal 20 may include call signal reception, message reception, a key signal input, a touch input, and the like.

The haptic unit 25d generates various tactile effects that user may feel. A typical example of the tactile effects generated by the haptic unit 25d is vibration. Strength, pattern and the like of the vibration generated by the haptic unit 25d is controllable.

The storage module 26 stores a program for operations of the terminal control module 28 and may temporarily store input/output data (for example, a phone book, messages, still images, moving images, and the like).

Furthermore, storage module 26 stores data related to vibrations and sounds in various patterns that are output from when a touch input is applied to a touch screen.

Furthermore, the storage module 26 stores source data for forming control-related information of the speaker device. Accordingly, the control-related data of the speaker device is configured in the form of image and sound. The process and result of generation of the control-related data of the speaker device is also stored.

The storage module 26 includes, for example, at least one type of a storage medium including a flash memory type, a hard disk type, a multimedia card micro type, a card type memory (for example, a SD memory, a XD memory or the like), RAM, SRAM, ROM, EEPROM, PROM, a magnetic memory, a magnet disk, and an optical disk.

The interface module 27 serves as an interface with all the external devices connected to the user terminal 20. The interface module 27 receives data from the external devices or power and transmits the data or power to internal components of the user terminal 20 or transmits data of the user terminal 20 to the external devices.

The terminal control module 28 usually controls the overall operation of the user terminal 20 and performs related controls and processing for, for example, voice calls, data communications, video calls, various applications running, and the like.

That is, the terminal control module 28 controls a control-related application program of the speaker device stored in the storage module 26 to be executed. The terminal control module also requests generation of control-related data of the speaker device and receives the generated control-related data of the speaker device, through execution of the control-related application program of the speaker device.

Furthermore, through execution of the control-related application program of the speaker device, the terminal control module 28 controls auxiliary elements including at least one of image, voice, and sound in the process of generating the control-related data of the speaker device desired by a user to be output through at least one of the display unit 25b and other output devices (for example, the sound output unit 25b, the alarm unit 25c, and the haptic unit 25d).

Furthermore, the terminal control module 28 constantly monitors a charging current and a charging voltage of a battery unit 29a and temporarily stores a monitoring value in the storage module 26. Herein, it is preferable that the storage module 26 stores not only battery charging state information such as the monitored charging current and charging voltage, but also battery specification information (product code, rating, and the like).

The power module 29 receives external power or internal power and supplies appropriate power required for operating respective components under control of the terminal control module 28. The power module 29 supplies power of the built-in battery unit 29a to respective components to be operated, and battery charging is possible using a charging terminal (not shown).

Various embodiments described herein may be implemented in a computer-readable or its similar medium using, for example, software, hardware, or any combination thereof.

For hardware implementation, embodiments described herein may be implemented by using at least one of application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, and electronic units for performing functions. In some cases, such embodiments may be implemented by the terminal control module 28.

For software implementation, embodiments such as procedures or functions described herein may be implemented with a separate software module performing at least one function or operation. Software codes may be implemented by a software application written in an appropriate software language. The software codes may be stored in the storage module 26 and executed by the terminal control module 28.

If the user terminal 20 is a smartphone, the smartphone is a phone based on an open operating system that has the freedom of downloading and deleting various application programs desired by a user, unlike a general handheld phone (referred to as a feature phone). That is, it is preferable that the smartphone denotes a communication device including a mobile phone not only having a general function, such as voice/video call and Internet data communication but also having a mobile office function, or all types of Internet phones or tablet PCs having Internet access without a voice call function.

The smartphone may be implemented to have various open operating systems mounted thereon. The open operating system includes Symbian of NOKIA, Blackberry of RIMS, iPhone of Apple, Windows Mobile of Microsoft, Android of Google, Bada of Samsung, and the like.

As such, the smartphone, which uses an open operating system, enables a user to randomly install and manage various application programs, unlike a mobile phone having a closed operating system.

The smartphone fundamentally includes a controller, a memory unit, a screen output unit, a key input unit, a sound output unit, a sound input unit, a camera unit, a wireless network communication module, a short-range wireless communication module, a battery for power supply, and the like.

The controller generally refers to functional elements for controlling operation of the smartphone and includes at least one processor and an execution memory. The controller is connected to each functional unit of the smartphone through a bus.

The controller loads at least one program code provided on the smartphone on the execution memory and processes the loaded program code through the processor and transmits a processing result to the at least one functional unit through the Bus, thus controlling operation of the smartphone.

The memory unit generally refers to non-volatile memories provided on the smartphone and functions to store and maintain at least one program code executed through the controller and at least one dataset used by the program code. The memory unit fundamentally stores a system program code and a system dataset each corresponding to an operating system of the smartphone, a communication program code and a communication data set configured to process a wireless communication connection of the smartphone, and at least one application program code and application dataset. A program code and a dataset for implementing the present invention are also stored in the memory unit.

The screen output unit is composed of a screen output device (for example, a liquid crystal display (LCD)) and an output module for driving the screen output device. The screen output unit is connected to the controller through a bus to output a processing result corresponding to a screen output among various processing results of the controller.

The key input unit is composed of a key input device (or a touch screen device that interworks with the screen output unit) having at least one key button, and an input module for driving the key input device. The key input unit is connected to the controller through a bus to receive input of a command for instructing various processing of the controller or data required for processing of the controller.

The sound output unit is composed of a speaker for outputting a sound signal and a sound module for driving the speaker. The sound output unit is connected to the controller through a bus such that a processing result corresponding to sound output among various processing results of the controller is output through the speaker. The sound module converts sound data to be output through the speaker into a sound signal by decoding the sound data.

The sound input unit is composed of a microphone for receiving a sound signal and a sound module for driving the microphone. The sound input unit transmits sound data input through the microphone to the controller. The sound module encodes the sound signal input through the microphone.

The camera unit is composed of an optical unit and a charge coupled device (CCD), and a camera module for driving the optical unit and the CCD. The camera unit obtains bitmap data input to the CCD through the optical unit. The bitmap data includes still image data and moving image data.

The wireless network communication module generally refers to a communication element that connects wireless communication and is composed of at least one of an antenna to transmit/receive a radio frequency signal at a certain frequency band, an RF module, a baseband module, and a signal processing module. The wireless network communication module is connected to the controller through a bus to transmit an operation result corresponding to wireless communication among various processing results of the controller via wireless communication, or to receive data via wireless communication and deliver the received data to the controller, while maintaining procedures of access, registration, communication, and handoff of the wireless communication.

Furthermore, the wireless network communication module includes a mobile communication element that performs at least one of an access to a mobile communication network, location registration, call process, call connection, data communication, and handoff according to the CDMA/WCDMA standards. Meanwhile, the wireless network communication module may further include a portable Internet communication element that performs at least one of access to a portable Internet, location registration, data communication, and hand off according to the IEEE 802.16 standards depending on the intention of those skilled in the art, and it should be understood that the present invention is not limited to a wireless communication element provided by the wireless network communication module.

The short-range wireless communication module is composed of a short-range wireless communication module that connects a communication session by using a radio frequency signal as a communication medium within a predetermined range. It is preferable that the short-range wireless communication module includes a RFID communication function according to the ISO 180000 standards, a Bluetooth communication function, a Wi-Fi communication function, and a public wireless communication function. Furthermore, the short-range wireless communication module may be integrated with the wireless network communication module.

The smartphone configured described above denotes a terminal capable of wireless communication. However, the smartphone may be provided using any device other than a smartphone as long as transmitting and receiving data through a network including the Internet. That is, the smartphone may include at least one of a notebook PC and a table PC having a short message transmission function and a network access function, and a portable terminal capable of being carried and moved.

While the exemplary embodiments of the portable Bluetooth speaker device having complex functions according to the invention have been described above, those skilled in the art will appreciate that various modifications, additions and substitutions are possible, without departing from the scope and spirit of the invention as disclosed in the accompanying claims. It is thus well known to those skilled in that art that the present invention is not limited to the embodiment disclosed in the detailed description, and the patent right of the present invention should be defined by the scope and spirit of the invention as disclosed in the accompanying claims.

INDUSTRIAL APPLICABILITY

The present invention can find wide application in portable Bluetooth speaker devices.

The invention claimed is:

1. A portable Bluetooth speaker device having complex functions, the speaker device comprising:
a Bluetooth receiver provided inside a main body that defines a body of the speaker device, and receiving voice information data from an external terminal via Bluetooth communication;
a GPS receiver provided inside the main body and receiving latitude, longitude, and altitude information using a plurality of global positioning system (GPS) satellites to obtain current location information data;
a carbon monoxide detector provided at a side of the main body and detecting carbon monoxide (CO) concentration in air;
a display unit provided at a side of the main body and displaying the current location information data obtained by the GPS receiver and a current carbon monoxide concentration value detected by the carbon monoxide detector on a display screen;
a power amplifier provided inside the main body and amplifying the voice information data received from the Bluetooth receiver to a predetermined amplification level;
a voice output unit provided at a side of the main body and outputting the amplified voice information data from the power amplifier;
a controller provided inside the main body, and configured to receive the voice information data from the Bluetooth receiver and transmit the received voice information data to the power amplifier such that a user can audibly perceive the voice information data through the voice output unit and to control such that the current location information data obtained by the GPS receiver and the current carbon monoxide concentration value detected by the carbon monoxide detector are displayed on the display screen of the display unit so as to be visually perceived by the user; and
a power supply unit provided inside the main body and supplying necessary power to the respective units,
wherein the control receives the current carbon monoxide concentration value detected by the carbon monoxide detector and compares the current carbon monoxide concentration value with a predetermined reference concentration value, and when the current carbon monoxide concentration value is greater than the reference concentration value, the controller controls operation of the power amplifier and the voice output unit to output a predetermined gas alarm sound at the predetermined amplification level, thus allowing the user to audibly perceive the alarm sound.

2. The speaker device of claim 1, wherein when the predetermined gas alarm sound is continuously output through the voice output unit for a predetermined period of time or longer, the controller controls operation of the power amplifier and the voice output unit to output the predetermined gas alarm sound at a maximum amplification level, thus allowing the user to perceive the predetermined gas alarm sound with help of people nearby.

3. The speaker device of claim 1, further comprising:
a user input unit provided at a side of the main body and outputting a specific user input signal in response to user manipulation,
wherein when the controller receives the specific user input signal from the user input unit while the predetermined gas alarm sound is output through the voice output, the controller controls operation of the power amplifier and the voice output unit such that output of the predetermined gas alarm sound is canceled.

4. The speaker device of claim 1, further comprising:
a user input unit provided at a side of the main body and outputting a specific user input signal in response to user manipulation; and
an LED lighting unit provided inside or outside the main body and outputting LED light having at least one color,
wherein the controller controls operation of the LED lighting unit such that a brightness or on-off state of the LED lighting unit is changed in response to a specific user input signal.

5. The speaker device of claim 1, further comprising:
an LED lighting unit provided inside or outside the main body and outputting LED light having at least one color; and
an illuminance sensor provided at a side of the main body and detecting external brightness information,
wherein the controller receives the external brightness information detected by the illuminance sensor, processes the detected external brightness information to obtain an external brightness value, and controls operation of the LED lighting unit such that the brightness or on-off state of the LED lighting unit is changed in response to the obtained external brightness value.

6. The speaker device of claim 1, further comprising:
a user input unit provided at a side of the main body and outputting a specific user input signal in response to user manipulation,
wherein the controller controls operation of the power amplifier and the voice output unit such that a predetermined distress occurrence signal is output through the voice output unit in response to a specific user input signal that is output from the user input unit when a distress occurs.

7. The speaker device of claim 1, wherein the power supply unit includes:
at least one battery; and
a charging circuit unit receiving external power through a charging terminal mounted at a side of the main body and charging the battery of the power supply unit under control of the controller.

8. The speaker device of claim 7, wherein the controller continuously monitors a battery power level of the power supply unit and controls such that the monitored battery power level is displayed on the display screen of the display unit.

9. The speaker device of claim 1, further comprising:
a user input unit provided at a side of the main body and outputting a specific user input signal in response to user manipulation; and
a wireless communication unit wirelessly transmitting a predetermined distress occurrence signal to the external terminal by using a wireless communication method,
wherein the controller controls operation of the wireless communication unit such that the predetermined distress occurrence signal is wirelessly transmitted to the external terminal in response to the specific user input signal output from the user input unit when a distress occurs, together with the current location information data obtained by the GPS receiver through the wireless communication unit.

10. The speaker device of claim 9, wherein the wireless communication method is any one of short-range wireless communication methods including Bluetooth, ZigBee, ultra-wideband (UWB), radio-frequency identification (RFID), and infrared (IR), or any one of long-range wireless communication methods including 3G, 4G, 5G, wireless fidelity (Wi-Fi), wireless gigabit alliance (WiGig), wireless broadband internet (Wibro), and world interoperability for microwave access (Wimax).

11. The speaker device of claim 1, wherein the external terminal is at least one of mobile terminal devices including a smartphone, a smart pad, and a smart note.

12. The speaker device of claim 1, further comprising:
a fine dust detector provided inside or outside the main body and detecting fine dust concentration in air; and
an ultrafine dust detector provided inside or outside the main body and detecting ultrafine dust concentration in air,
wherein the controller controls such that a current fine dust concentration value and a current ultrafine dust concentration value, which are respectively detected by the fine dust detector and the ultrafine dust detector, are displayed on the display screen of the display unit so as to be visually perceived by the user.

13. The speaker device of claim 12, wherein the fine dust detector measures fine dust having a particle size of equal to or less than 10 μm, and the fine dust detector includes at least one sensor for measuring at least one of air pollutants including sulfur dioxide, nitrogen oxide, lead, and ozone, and
the ultrafine dust detector measures ultrafine dust having a particle size of equal to or less than 2.5 μm, and the ultrafine dust detector includes at least one ultrafine dust sensor for measuring total carbon, organic carbon, and elemental carbon contained in ultrafine dust.

* * * * *